(12) United States Patent
Wittorff

(10) Patent No.: US 11,096,894 B2
(45) Date of Patent: *Aug. 24, 2021

(54) ORAL TABLET FOR INDUCED SALIVA GENERATION

(71) Applicant: Fertin Pharma A/S, Vejle (DK)

(72) Inventor: Helle Wittorff, Vejle Ost. (DK)

(73) Assignee: Fertin Pharma A/S

(*) Notice: Subject to any disclaimer, the term of this patent is extended or adjusted under 35 U.S.C. 154(b) by 55 days.

This patent is subject to a terminal disclaimer.

(21) Appl. No.: 15/982,758

(22) Filed: May 17, 2018

(65) Prior Publication Data

US 2019/0350859 A1 Nov. 21, 2019

(51) Int. Cl.
  A61K 9/18 (2006.01)
  A61K 9/20 (2006.01)
  A61P 1/02 (2006.01)
  A61K 9/00 (2006.01)
  A61K 45/06 (2006.01)

(52) U.S. Cl.
  CPC .......... *A61K 9/2018* (2013.01); *A61K 9/0056* (2013.01); *A61K 45/06* (2013.01); *A61P 1/02* (2018.01); *A61K 9/2054* (2013.01); *A61K 9/2086* (2013.01)

(58) Field of Classification Search
  None
  See application file for complete search history.

(56) References Cited

U.S. PATENT DOCUMENTS

| | | |
|---|---|---|
| 4,627,977 A | 12/1986 | Gaffar et al. |
| 4,820,506 A | 4/1989 | Kleinberg et al. |
| 5,576,014 A | 11/1996 | Mizumoto et al. |
| 5,874,068 A | 2/1999 | Engelman et al. |
| 6,024,981 A | 2/2000 | Khankari et al. |
| 6,146,661 A | 11/2000 | Hoshino |
| 7,067,149 B1 | 6/2006 | Chauveau et al. |
| 8,435,542 B2 | 5/2013 | Manley et al. |
| 8,658,139 B1 | 2/2014 | Cutler |
| 2003/0022912 A1 | 1/2003 | Martino et al. |
| 2003/0215502 A1* | 11/2003 | Pruss .................. A61K 9/0056 424/465 |
| 2006/0063189 A1 | 6/2006 | Fankhauser |
| 2008/0107729 A1* | 5/2008 | Amin .................. A61K 9/2018 424/465 |
| 2009/0311320 A1 | 12/2009 | Oury et al. |
| 2011/0123462 A1 | 5/2011 | Mordas et al. |
| 2011/0250247 A1 | 10/2011 | Boghmans et al. |
| 2013/0302387 A1 | 11/2013 | Pedersen |
| 2014/0328973 A1 | 11/2014 | Nielsen |
| 2015/0101627 A1 | 4/2015 | Marshall et al. |
| 2016/0120793 A1 | 5/2016 | Abdalla et al. |
| 2016/0145203 A1 | 5/2016 | Gambogi et al. |
| 2018/0140521 A1 | 5/2018 | Geonnotti et al. |
| 2018/0140554 A1 | 5/2018 | Wittorff |
| 2018/0140591 A1 | 5/2018 | Wittorff et al. |

FOREIGN PATENT DOCUMENTS

| | | |
|---|---|---|
| CN | 1709229 A | 12/2005 |
| EP | 0413427 A2 | 2/1991 |
| EP | 0497439 A1 | 8/1992 |
| EP | 0913148 A1 | 5/1999 |
| EP | 0922464 A1 | 6/1999 |
| EP | 1369109 A1 | 12/2003 |
| GB | 1526020 A1 | 9/1978 |
| WO | 9932092 A1 | 7/1999 |
| WO | 02102357 A1 | 12/2002 |
| WO | 2004068964 A1 | 8/2004 |
| WO | 2009007768 A1 | 1/2009 |
| WO | 2009016133 A1 | 2/2009 |
| WO | 2009080023 A1 | 7/2009 |
| WO | 2010104563 A2 | 9/2010 |
| WO | 2012085043 A2 | 6/2012 |
| WO | 2013125350 A1 | 8/2013 |
| WO | 2016061486 A1 | 4/2016 |
| WO | 2018091048 A1 | 5/2018 |
| WO | 2018091050 A1 | 5/2018 |
| WO | 2018093501 A1 | 5/2018 |

OTHER PUBLICATIONS

C. Morris (ed.) "Module" In Academic press Dictionary of science and technology. Oxford, United Kingdom: Elsevier Science & Technology, 1992. 2 pages. Available from http://search.credoreference.com/content/entry/apdst/module/0.

European Patent Office, Search Report and Written Opinion for International Application No. PCT/DK2019/050152 (11 pages), dated Aug. 22, 2019.

European Patent Office, Search Report and Written Opinion for International Application No. PCT/DK2019/050157 (11 pages), dated Sep. 16, 2019.

European Patent Office, Search Report and Written Opinion for International Application No. PCT/DK2019/050158 (11 pages), dated Aug. 22, 2019.

European Patent Office, Search Report and Written Opinion for International Application No. PCT/DK2019/050159 (11 pages), dated Aug. 22, 2019.

European Patent Office, Search Reportand Written Opinion for International Application No. PCT/DK2019/050154 (12 pages), dated Sep. 20, 2019.

European Patent Office, Search Report and Written Opinion for International Application No. PCT/DK2019/050155 (12 pages), dated Sep. 20, 2019.

(Continued)

*Primary Examiner* — David J Blanchard
*Assistant Examiner* — Daniel F Coughlin
(74) *Attorney, Agent, or Firm* — St. Onge Steward Johnston & Reens LLC

(57) ABSTRACT

The invention relates to an oral tablet suitable for active pharmaceutical ingredients comprising a population of particles, the population of particles comprising directly compressible (DC) and non-directly compressible (non-DC) sugar alcohol particles, the non-DC particles providing the tablet with a plurality of discrete non-DC areas, and the non-DC areas resulting in induced saliva generation upon mastication of the tablet.

19 Claims, 3 Drawing Sheets

(56) References Cited

OTHER PUBLICATIONS

European Patent Office, Search Report and Written Opinion for International Application No. PCT/DK2019/050156 (17 pages), dated Sep. 20, 2019.
European Patent Office, Search Report and Written Opinion for International Application No. PCT/DK2019/050160 (17 pages), dated Sep. 20, 2019.
European Patent Office, Search Report and Written Opinion for International Application No. PCT/DK2019/050153 (18 pages), dated Oct. 7, 2019.
Bolhuis, Gerad K., Erik G. Rexwinkel, and Klaas Zuurman. "Polyols as filler-binders for disintegrating tablets prepared by direct compaction." Drug development and industrial pharmacy 35.6 (2009): 671-677.
Weseel, Stefan W., et al. "Potential benefits of chewing gum for the delivery of oral therapeutics and its possible role in Oral healthcare." Expert opinion on drug delivery 13.10 (2016): 1421-1431.
Roquette Sweetpearl; Maltitol USP/NF, EP; Signet Chemical Corporation Pvt. Ltd.; Products webpage; Retrieved from internet on May 13, 2019; www.signetchem.com/product.aspx?prdid=1044.

* cited by examiner

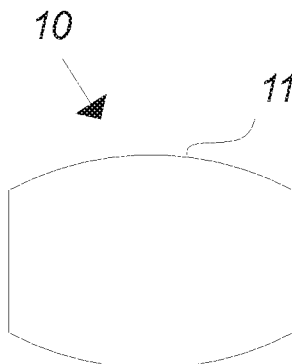
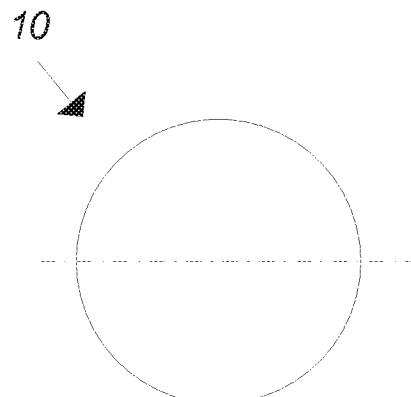
Fig.1a　　　Fig.1b
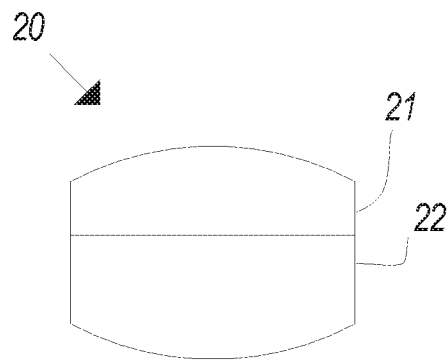
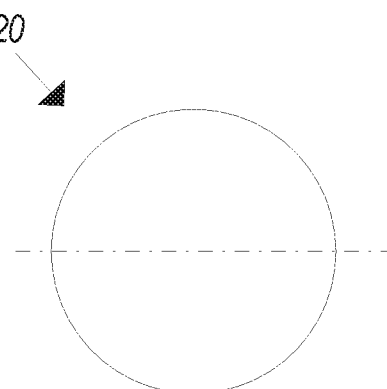
Fig.2a　　　Fig.2b
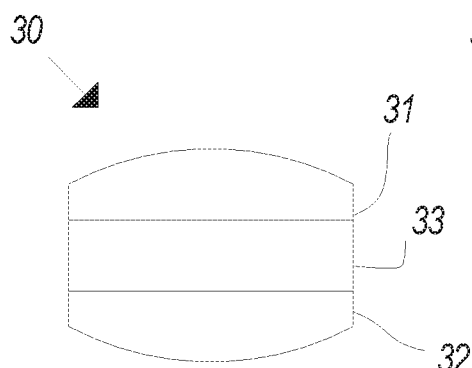
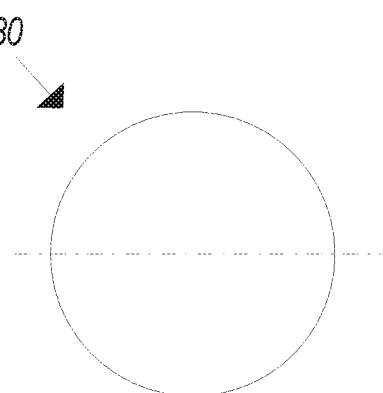
Fig.3a　　　Fig.3a

ORAL TABLET FOR INDUCED SALIVA GENERATION

FIELD OF THE INVENTION

The invention relates to an oral tablet for induced saliva generation. In particular, the oral tablet is suitable for delivery of active pharmaceutical ingredients.

BACKGROUND OF THE INVENTION

In the prior art it is well-known with chewable tablets and lozenges where a substantial part of the delivery vehicle is comprised of a sugar alcohol. It is also well-known that such delivery vehicles may be applied for delivery of active ingredients.

A challenge related to such delivery vehicles is that the user is more and more focused on convenience and extended functionality. Such requirements do very often conflict with what is technically possible.

EP application 0 922 464 A1 discloses a quickly disintegrable compression-molded material such as tablets produced through conventional tableting processes. The tablets comprise granulated erythritol and exhibits rapid disintegration and dissolution when placed in the oral cavity or water.

EP 0 922 464 is thus a representative example of one of many references using granulated polyols, such as erythritol for compressed tablets.

It is an object of the invention to obtain an oral tablet which is able to promote salivation generation.

SUMMARY OF THE INVENTION

The invention relates to an oral tablet suitable for active pharmaceutical ingredients comprising a population of particles, the population of particles comprising directly compressible (DC) and non-directly compressible (non-DC) sugar alcohol particles, the non-DC particles providing the tablet with a plurality of discrete non-DC areas, and the non-DC areas resulting in induced saliva generation upon mastication of the tablet.

One advantage of the invention is a surprisingly strong saliva generation compared to conventional chewable tablets and lozenges. Particularly, the plurality of non-DC areas provided in the tablet surprisingly induces a remarkable generation of saliva. Having a combination of non-DC particles and DC particles in the population of particles may further facilitate sufficient mechanical strength combined with stability of the tablet, disintegrability of the tablet upon chewing, and induced saliva generation upon chewing.

One un-expected advantage over the prior art is that the saliva generation is surprisingly sustained even after a user has swallowed the bulk-portion of the non-DC sugar alcohols. This sustaining of the salivation generation may be advantageous in relation to many applications of an oral tablet ranging from mouthfeel, taste, flavor perception, etc.

Moreover, a delivery platform suitable for active ingredients is provided. The oral tablets may be highly suitable as the delivery platform, e.g. due to superior saliva generation induced by the non-DC areas. Alternatively, the oral tablet may be used as e.g. a confectionary tablet, without inclusion of active pharmaceutical ingredients.

It is noted that in the present context, the oral tablet comprises the population of particles, whereas the population of particles comprises the directly compressible (DC) and the non-directly compressible (non-DC) sugar alcohol particles.

In the present context, the non-DC sugar alcohol particles are understood and defined by the skilled person with reference to their typical commercial trade grade.

In an embodiment of the invention, the non-DC sugar alcohol particles have not been granulated prior to tableting.

Thus, the non-DC sugar alcohol particles are provided as non-granulated particles.

These are typically available in a non-DC form of the relevant sugar alcohol as particles which have not been preprocessed by granulation with other sugar alcohols or binders for the purpose of obtaining so-called direct compressible particles (DC) on the basis of sugar alcohol particles which are by themselves not suitable for direct compression. Such non-DC particles of sugar alcohol may typically consist of the sugar alcohol. Therefore, non-DC sugar alcohol particles may typically be particles consisting of sugar alcohol, which is non-directly compressible in its pure form. Examples of sugar alcohols which are non-directly compressible when provided as particles consisting of the sugar alcohol in question include erythritol, xylitol, maltitol, mannitol, lactitol, isomalt, etc.

Therefore, preferred non-DC grades of sugar alcohol may include pure sugar alcohol particles.

In an embodiment of the invention, the population of particles is tableted into a first module and combined with a second population of particles that is tableted into a second module.

Thus, a synergy between utilization of non-DC sugar alcohol particles as a disintegration promoter due to the lower mechanical strength and also as a salivation promoter in combination with a second module, which can provide additional mechanical strength, thereby acting as a carrier module. This is especially advantageous when the second population of particles contributes to an attractive mouthfeel by a high content of DC sugar alcohols, which also provides mechanical strength to the tablet.

One advantage of the above embodiment may be that the second module may have a higher mechanical strength, e.g. by means of a different composition comprising e.g. a very large amount of direct compressible ingredients, such as DC sugar alcohols.

A further advantage of the above embodiment may be that the second module may have a higher loading capacity for e.g. active ingredients, partly due to the higher obtainable mechanical strength achievable by large amounts of direct compressible ingredients, such as DC sugar alcohols.

Thus, in the above embodiment said population of particles is tableted into a first module, and wherein the tablet further comprises a second population of particles that is tableted into a second module. The first module may be tableted before the second module, or vice versa. In some embodiments, the tablet may comprise one or more further modules.

In an embodiment of the invention the oral tablet comprises at least two modules. A tablet comprising two or more modules will have module sizes which each are comparable to the volume of the complete tablet. Comparable in the present context means that the modules are not understood as small particles and a module should at least be greater than $1/20$ of the complete tablet volume, preferably greater than $1/10$ of the complete tablet volume.

The module may typically be gathered from a plurality of compressed particles and have a weight which is greater than 0.2 gram and less than 10 grams.

In an embodiment of the invention a module is defined as a plurality of particles being compressed together to form a gathered module of particles.

In an embodiment of the invention the oral tablet comprises a plurality of oral tablet modules. In the present context the application of e.g. two modules are in particular advantageous as the use of non-DC sugar alcohols by nature may result in a more fragile tablet or at least the module in which the non-DC sugar alcohols are. In other words, non-DC sugar alcohols may be present primarily in one module thereby optimizing the desired salivation and sensory experience from the module and the tablet as such whereas another module may serve as a support ensuring that the desired stability and friability of the complete tablet is obtained.

In an embodiment of the invention the plurality of modules are slice-like layers. The term "slice-like" layer is a plain but very precise way of to the skilled person how a module may be provided, as such a layer is a standard structure obtained through conventional tableting procedures.

According to an embodiment of the invention, the tablet has two modules. Optionally, a coating may be applied around the two modules to form the final tablet.

An advantage of using two modules is described above, but it should also be noted that this effect may also be obtained when applying layers of very different nature. Such application may e.g. include the use of a gum module and a non-gum module, where the non-gum modules are containing the non-DC sugar alcohol particles. In this way, the non-gum layer may release the advantageous non-DC sugar alcohols and the gum layer may both stabilize the tablet as described above but also interact with the non-DC sugar alcohols during in particular the initial release for establishment of a very pleasant and impressing initial chew phase. This includes an increased saliva and moisture experience.

In an embodiment of the invention said population of particles is tableted into a first module and combined with a second population of particles that is tableted into a second module, where the second population of particles is different from the first population of particles.

In an embodiment of the invention said population of particles is tableted into a first module and combined with a second population of particles that is tableted into a second module, where the second population of particles is different from the first population of particles, where the second population of particles is free of non-DC sugar alcohols.

In one embodiment, the second population of particles comprises a large amount of DC sugar alcohols, such as larger amounts than the first population of particles. For example, the second population of particles may comprise at least 30% by weight of DC sugar alcohols, such as at least 50% by weight of DC sugar alcohols, such as at least 70% by weight of sugar alcohols. In an example embodiment, the second population of particles may comprise between 50 and 99.9% by weight of sugar alcohols, such as between 70 and 99% by weight of sugar alcohols.

The amount of DC sugar alcohol may depend on the type and amount of active ingredient applied in the tablet.

In an embodiment of the invention the second module is tableted before the first module.

In an embodiment of the invention, the non-DC areas are evenly distributed in the tablet or at least one module of the tablet.

One advantage of the above embodiment may be that the even distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the even distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the even distribution to facilitate effect dispersion of mastication fragments in the oral cavity upon mastication.

In an embodiment of the invention, a series of at least 10 of said tablets comprises said non-DC particles in an amount varying with a relative standard deviation (RSD) below 10%.

One advantage of the above embodiment may be that uniform product may be obtained having low variation in the amount of non-DC sugar alcohol between tablets. Consequently, the functionality provided by non-DC areas in the tablet may provide low variation between tablets.

It is noted that the reference to RSD and a sequence of tablets typically refers to a tablet series of a production line.

Furthermore, the RSD of the non-DC sugar alcohol between tablets is a measure of the degree of even distribution of the non-DC areas. Therefore, having an RSD below 10% in a series of at least 10 tablets indicates an even distribution of the non-DC areas. Having evenly distributed non-DC areas facilitates a high salivation since the non-DC areas are effectively distributed in the mouth upon mastication and a resulting disintegration of the tablet.

According to an embodiment of the invention, the amount of non-DC particles between a series of at least 10 of the tablets holds a relative standard deviation (RSD) below 5%.

An advantageous method of dosing non-DC sugar alcohols into a composition for a large number of tablets has been established, which facilitates an exact dosing of the non-DC sugar alcohols in a series of tablets. This means that large-scale production of tablets comprising non-DC sugar alcohols is made possible with improved results concerning distribution of the non-DC areas in the tablets and thereby an improved RSD between the tablets of a series.

The term RSD as used herein is short for the relative standard deviation, which within this present field is used to indicate the uniformity in content of non-DC sugar alcohols in a series of tablets. An analysis may be carried out on an array of 10 tablets of a series, wherein the content of the non-DC sugar alcohols in question is measured. From these values the RSD may be calculated through the standard formula of $$\text{RSD} = (\text{standard deviation of array } X) * 100\% / (\text{average of array } X).$$

In some cases, it may be most convenient to measure RSD of the amount of non-DC sugar alcohol particles indirectly. For example, the RSD of another ingredient may be used as an indicator for the amount of non-DC sugar alcohol particles, as segregation affects the whole composition of the tablet or module in question.

When attempting to obtain a high degree of even distribution of the non-DC areas, insufficient mixing may lead to uneven distribution, such as undesirable agglomeration of particles within certain parts of the tablet. Also, even if mixing very thoroughly the ingredients, an undesirable handling of the mixture from the mixing to a tableting machine may lead to segregation. For example, smaller particles may typically segregate to the bottom part of a container, thereby leading to different particle distributions for different tablets. Particularly when the different ingredients have different particle sizes, e.g. if non-DC particles have a larger particle size compared to other ingredients, segregation may lead to different contents of non-DC sugar alcohols in different tablets. Yet, another aspect is that even storing a thoroughly mixed composition for too long may lead to segregation.

On the other hand, a measure of having obtained even distribution of non-DC areas in at least one module of the tablet may be that a series of at least 10 of the tablets holds a relative standard deviation (RSD) below 10% with respect to the non-DC sugar alcohol content.

In is noted that the term segregation as used herein would be known to the skilled person to mean the separation of a mixture according to similarity, typically size. This may in the present context be a problem when handling a mixture comprising very different sizes of particles, e.g. in a hopper for holding and feeding the composition via a feeding mechanism to a die cavity.

Particularly, when including an active ingredient in the tablet, having a low RSD on the content of such active ingredients is highly desirable.

In an embodiment of the invention, the non-DC areas are homogenously distributed in the tablet or at least one module of the tablet.

One advantage of the above embodiment may be that the homogenous distribution of the non-DC areas promotes an effective disintegration of the module upon mastication, e.g. due to lower mechanical strength contribution from the non-DC particles, thereby facilitating effective contacting of the resulting mastication fragments formed by the mastication with saliva, again increasing dissolving of the tablet. Also, the homogenous distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the homogenous distribution to facilitate effect dispersion of mastication fragments in the oral cavity upon mastication.

In an embodiment of the invention, the tablet is a chewable tablet.

In an embodiment of the invention, at least 10% by weight of said population of particles have a particles size below 250 µm, and wherein at least 30% by weight of said population of particles have a particles size above 500 µm.

According to an embodiment of the invention, the population of particles have a particle size distribution with a full width at half maximum (FWHM) of at least 100 µm.

Particularly when having a broad particle size distribution of the population of particles, it was surprising to the inventor that even distribution of the non-DC areas could be accomplished. Typically, when having a broad particle size distribution, such as when having a width from the 10% quantile to the 90% quantile greater than 30% of the mean value, associated compositions are considered vulnerable to segregation. However, according to an embodiment of the invention, the non-DC areas are evenly distributed in at least one module of the tablet and may have amounts of non-DC particles between a series of at least 10 of the tablets holding a relative standard deviation (RSD) below 10%.

According to an embodiment of the invention, the non-DC particles have an average non-DC particle size at least 50 µm larger than an average DC particle size of the DC particles.

In an embodiment of the invention, the non-DC sugar alcohol particles are selected from non-DC particles of erythritol, maltitol, xylitol, isomalt, lactitol, mannitol, and combinations thereof.

One advantage of the above embodiment may be that a desirable induced saliva generation is obtained.

According to an embodiment of the invention, the non-DC sugar alcohol particles consist of sugar alcohols selected from erythritol, maltitol, xylitol, isomalt, lactitol, mannitol, and combinations thereof.

In an embodiment of the invention, the non-DC sugar alcohol particles are selected from non-DC particles of erythritol, maltitol, xylitol, isomalt, and combinations thereof.

One advantage of the above embodiment may be that a desirable induced saliva generation is obtained.

In an embodiment of the invention, the non-DC sugar alcohol particles are selected from non-DC particles of erythritol, maltitol, xylitol, and combinations thereof.

One advantage of the above embodiment may be that a desirable induced saliva generation is obtained. Also, when a cooling sensation is desirable, having non-DC sugar alcohol particles comprising or consisting of erythritol, xylitol, or combinations thereof advantageous.

In an embodiment of the invention, the non-DC sugar alcohol particles are non-DC erythritol particles.

One advantage of the above embodiment may be that a desirable induced saliva generation is obtained, together with a cooling sensation.

In an embodiment of the invention, the non-DC sugar alcohol particles are non-DC xylitol particles.

One advantage of the above embodiment may be that a desirable induced saliva generation is obtained, together with a cooling sensation.

In an embodiment of the invention, the tablet comprises said non-DC sugar alcohol particles in an amount of at least 10% by weight of the tablet.

In an embodiment of the invention, said DC sugar alcohol particles comprises sugar alcohols selected from DC particles of sorbitol, erythritol, xylitol, lactitol, maltitol, mannitol, isomalt, and combinations thereof.

Sorbitol is an example of a sugar alcohol, which is considered DC grade, when provided as particles consisting of sorbitol, i.e. in its pure form. On the other hand, several other sugar alcohols are considered non-DC grade if providing them as particles consisting of the specific sugar alcohol. Therefore, such non-DC sugar alcohols are conventionally processed into DC grade sugar alcohols, e.g. by granulating them with e.g. a binder.

Examples of trade grades of DC sugar alcohols include sorbitol particles provided as e.g. Neosorb P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab 200 from Dupont.

In an embodiment of the invention, the tablet comprises said DC sugar alcohol particles in an amount of at least 10% by weight of the tablet.

According to an embodiment of the invention, said population of particles comprises DC sugar alcohol particles in an amount of at least 10% by weight.

According to an embodiment of the invention, the first module comprises DC sugar alcohol particles in an amount of at least 10% by weight.

In an embodiment of the invention, the second module comprises DC sugar alcohol particles in an amount of at least 30% by weight of the second module.

In an embodiment of the invention, the second module comprises DC sugar alcohol particles in an amount of at least 50% by weight of the second module.

In an embodiment of the invention the DC sugar alcohol particles in the second module are selected from DC particles of sorbitol, erythritol, xylitol, lactitol, maltitol, mannitol, isomalt, and combinations thereof.

In an embodiment of the invention, friability of the tablet is less than 3%, such as less than 2%, such as less than 1.5%, wherein friability is measured according to European Pharmacopoeia 9.1, test method 2.9.7. by using a pharmaceutical friability-tester PTF 10E from Pharma Test.

One advantage of the above embodiment may be that a tablet with a relatively high mechanical stability is obtained, while at the same time having the desirable mouthfeel of the invention.

According to an embodiment of the invention, friability of the tablet is between 0.2% and 3%, such as between 0.2% and 2%, wherein friability is measured according to European Pharmacopoeia 9.1, test method 2.9.7. by using a pharmaceutical friability-tester PTF 10E from Pharma Test.

In an embodiment of the invention, the tablet comprises one or more binders other than binders forming part of the DC sugar alcohol particles in an amount of 0.1 to 6% by weight of the tablet.

Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

According to an embodiment of the invention, the one or more binders comprises one or more cellulose binders.

In an embodiment of the invention the one or more binders comprises microcrystalline cellulose (MCC), hydroxypropyl cellulose (HPC) or hydroxypropylmethyl cellulose (HPMC) or any combination thereof.

In an embodiment of the invention the oral tablet comprises hydroxypropyl cellulose (HPC) binder in the amount of 0.1 to 6% by weight of the tablet, such as 0.1 to 5%, such as 0.1 to 4%, such as 0.1 to 3%, such as 0.1 to 2% by weight of the tablet.

HPC may be applied as a particular attractive binder. Thus, this binder, when used with non-DC sugar alcohols such as erythritol, exhibits an advantageous sensory experience when compared to other well-known binders. In particular, the user of HPC lower than 4% by weight of the tablet is advantageous, such as 0.1 to 3%, such as 0.1 to 2% by weight of the tablet.

In an embodiment of the invention the non-DC sugar alcohol particles are particles that are not granulated, and the one or more binders are present as separate components in the tablet.

In an embodiment of the invention the non-DC sugar alcohol particles are particles consisting of the sugar alcohol and the particles are not pre-granulated together with the one or more binders that are present in the tablet as separate components.

It is noted that the use of binders as particles separate from the non-DC particles does not compromise the advantageous sensory properties even when applying a firm pressure tableting force, whereas the granulation with the binder to the sugar alcohol clearly reduces the desired sensory properties.

In an embodiment of the invention, the resistance to crunching of the tablet is greater than 60N, such as greater than 70N, such as greater than 80N, such as greater than 90N, such as greater than 100 N, such as greater than 110, such as greater than 130N such as greater than 150N, wherein the resistance to crunching of the tablet is less than 300N, such as less than 250N, such as less than 200N, wherein the resistance to crunching is determined according to European Pharmacopoeia 9.1, test method 2.9.8. by using a pharmaceutical resistance to crunching tester model Pharma Test type PTB 311.

According to an embodiment of the invention, the tablet comprises at least one module, the module comprising more than 10% by weight of compressed non-DC sugar alcohol particles, the resistance to crunching of the module being greater than 60N, such as greater than 70N, such as greater than 80N, such as greater than 90N such as greater than 100 N, where the resistance to crunching is determined according to the European Pharmacopoeia 9.1, test method 2.9.8. by using a pharmaceutical resistance to crunching tester model Pharma Test type PTB 311.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the formulation.

In an embodiment of the invention, the tablet has a weight ratio between said non-DC sugar alcohol particles and said DC sugar alcohol particles, which is between 0.3 and 0.7.

The weight ratio between non-DC sugar alcohol particles and DC sugar alcohol particles have proven significant according to an embodiment of the invention in the sense that a relatively high amount of non-DC sugar alcohol particles must be present in order to obtain the mouthfeel and taste obtained through the invention. However, this taste and mouthfeel also resides in the DC sugar alcohol particles. An example of such DC sugar alcohol particle is DC grade xylitol, which, together with the non-DC sugar alcohol particles may provide a mouthfeel which is unique and very attractive to test panels.

The weight ratio between non-DC sugar alcohol particles and DC sugar alcohol particles have proven significant as mentioned above in relation to the direct sensation and mouthfeel experienced by the user but is has moreover addressed the challenge in relation to mouthfeel when DC sugar alcohol particles crumbles during the initial chew. The mechanical stability of the tablet is much desired when the tablet is in its non-chewed form, but a fast disintegration and dissolving is desirable when the tablet is chewed due to the fact that user of the tablet dislike a sandy mouthfeel induced through small hard-pressed crumbles of DC sugar alcohol. The use of a very high amount of non-DC sugar alcohol particles will facilitate a perceived fast dissolving and disintegration of the tablet after the initial chews.

According to an embodiment of the invention the tablet has a weight ratio between said non-DC sugar alcohol particles and said DC sugar alcohol particles, which is greater than 0.3, such as greater than 0.4, such as greater than 0.5.

According to an embodiment of the invention the tablet has a weight ratio between said non-DC sugar alcohol particles and said DC sugar alcohol particles, which is smaller than 0.7, such as smaller than 0.6, such as smaller than 0.55.

The weight ratio between non-DC sugar alcohol particles and DC sugar alcohol particles is important for the purpose of obtaining an advantageous taste and mouthfeel. By having an upper limit of this weight ratio, the chewer will moreover also experience a desirable crunch sensation when starting masticating the tablet, the crunch being obtained through the use of substantial amounts of DC sugar alcohol particles and the non-DC sugar alcohol particles.

According to an embodiment of the invention, the tablet comprises the non-DC sugar alcohol particles in an amount of greater than 0.3 gram.

According to an embodiment of the invention, the weight of non-DC sugar alcohol particles contained in the tablet is greater than greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC sugar alcohol particles is relatively high. It is in particular high when considering that the non-DC sugar alcohol in conventional sense is not regarded attractive for compression, but the mouthfeel and salivation perceived by the user is there improved significantly, when compared to low amounts or the same amounts of DC sugar alcohol.

According to an embodiment of the invention, the tablet comprises the non-DC sugar alcohol particles in an amount of less than 3.0 gram, such as less than 2.0 gram, such as less than 1.5 gram.

In an embodiment of the invention wherein the tablet has a weight of between 0.5 and 4.0 grams.

In an embodiment of the invention, saliva generation upon mastication of the tablet is induced compared to a tablet without non-DC sugar alcohol particles.

In an embodiment of the invention, saliva generation upon mastication of the tablet is induced compared to a tablet where the discrete areas are based on DC sugar alcohol particles.

In an embodiment of the invention, the tablet generates more than 1.5 mL saliva within 30 seconds from onset of mastication.

According to an embodiment of the invention the discrete non-DC areas induces saliva generation of more than 2.0 mL saliva within 30 seconds from onset of mastication.

According to an embodiment of the invention the discrete non-DC areas induces saliva generation of more than 3.0 mL saliva within 30 seconds from onset of mastication.

In an embodiment of the invention, the tablet generates more than 1.5 mL saliva within a period from 30 to 90 seconds from onset of mastication.

According to an embodiment of the invention the discrete non-DC areas induces saliva generation of more than 2.0 mL saliva within 30 to 90 seconds from onset of mastication.

In an embodiment of the invention, the tablet generates more than 1.5 mL saliva within a period from 90 to 180 seconds from onset of mastication.

In an embodiment of the invention, the tablet generates more than 1.5 mL saliva within a period from 180 to 300 seconds from onset of mastication.

In an embodiment of the invention, the tablet comprises flavor.

The amount of flavor may e.g. be from 0.1 to about 10% by weight of the tablet, such as 0.1 to about 6% by weight of the tablet.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

In an embodiment of the invention, the tablet comprises an active ingredient.

According to an embodiment of the invention the active ingredient is included in the population of particles.

According to an embodiment of the invention the active ingredient is included in the second population of particles.

In an embodiment of the invention, the tablet comprises an active pharmaceutical ingredient.

According to an embodiment of the invention the active pharmaceutical ingredient is included in the population of particles.

According to an embodiment of the invention the active pharmaceutical ingredient is included in the second population of particles.

In an embodiment of the invention, the population of particles comprises particles comprising gum base, and wherein the tablet is designed to be masticated into a coherent residual containing water-insoluble components.

The application of gum may in the present context may invoke a delay of release for active ingredients and this may again promote the buccal and upper throat absorption of active pharmaceutical ingredient when this is released from the oral tablet during mastication.

In an embodiment of the invention, the oral tablet contains particles comprising gum base, and wherein the gum base comprises at least 5% by weight of elastomer.

The specific use of a relatively high proportion of elastomer in the gum base may effectively be used for modification of the release of active ingredients in terms of time and amount and the elastomer may also provide robust structure of the tablet facilitating that it is chewed into a coherent residual containing water-insoluble components. Some active ingredient may risk invoking disintegration of the residual whereas an elastomer may increase the coherence and compensate for the aggressive active ingredients.

In an embodiment of the invention the gum base comprises at least 10% by weight of elastomer.

In an embodiment of the invention the gum base comprises at least 15% by weight of elastomer.

In an embodiment of the invention the gum base comprises between 15% and 25% by weight of elastomer.

In an embodiment of the invention the gum base comprises between 17% and 23% by weight of elastomer.

In an embodiment of the invention, the tablet is free of gum base.

In an embodiment of the invention, the tablet dosage form is for use in buccal absorption of active ingredients.

In an embodiment of the invention, the oral tablet comprises tooth paste in the amount of at least 0.1% by weight of the oral tablet.

In an embodiment of the invention the oral tablet comprises dentifrice in the amount of at least 0.1% by weight of the oral tablet.

In an embodiment of the invention the oral tablet comprises dentifrice in the amount of at least 0.1% by weight of the oral tablet, and the population of particles comprises particles comprising gum base.

In an embodiment of the invention the oral tablet comprises dentifrice in the amount of at least 0.1% to 25% by weight of the oral tablet excluding abrasive.

In an embodiment of the invention the oral tablet comprises tooth paste in the amount of at least 0.1% to 25% by weight of the oral tablet excluding abrasive.

Dentifrice or tooth paste will typically comprise at least one of the below active ingredients.

In an embodiment of the invention the active ingredient comprises one or more oral care agents.

In an embodiment of the invention the active ingredient comprises one or more anti-plaque agents.

Anti-plaque agents include fluoride ion sources. Anti-plaque agents are any substance which by itself acts to inhibit the accumulation of bacterial deposits on the surfaces of the oral cavity. Examples include xylitol and other anti-microbial agents. The inhibition effects of the xylitol on oral microbes may have better effect when used in conjunction with an extract since the extract is also acting to disable the microbes.

Typical examples of active ingredients that are particularly desirable from considerations of anti-plaque effectiveness, safety and formulation are:

Naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, .beta.-lactamase inhibitors; meziocillin, piperacillin, aztreonam, norfloxacin, trimethoprim, ceftazidime, dapsone. Halogenated diphenyl ethers, e.g. 2',4,4'-trichloro-2-hydroxydiphenyl ether (Triclosan), 2,2'-dihydroxy-5,5'-dibromo-diphenyl ether. Halogenated salicylanilides, e.g. 4',5-dibromosalicylanilide, 3,4',5-trichloro-salicylanilide, 3,4',5-tribromo-salicylanilide, 2,3,3',5-tetrachloro-salicylanilide, 3,3,3',5-tetrachloro-salicylanilide, 3,5-dibromo-3'-trifluoromethyl-salicylanilide, 5-n-octanoyl-3'-trifluoromethyl-salicylanilide, 3,5-dibromo-4'-trifluoromethyl-salicylanilide, 3,5-dibromo-3'-trifluoromethyl-salicylanilide (Flurophene). Benzoic esters, e.g. methyl-p-hydroxybenzoic ester, ethyl-p-hydroxybenzoic ester, propyl-p-hydroxybenzoic ester, butyl-p-hydroxybenzoic ester. Halogenated carbanilides, e.g. 3,4,4'-trichlorocarbanilide, 3-trifluoromethyl-4,4'-dichlorocarbanilide, or 3,3,4'-trichlorocarbanilide. Phenolic compounds (including phenol and its homologs, mono- and poly-alkyl and aromatic halophenol and their homologs), e.g. phenol, 2-methyl-phenol, 3-methyl-phenol, 4-methyl-phenol, 4-ethyl-phenol, 2,4-dimethyl-phenol, 2,5-dimethyl-phenol, 3,4-dimethyl-phenol, 2,6-dimethyl-phenol, 4-n-propyl-phenol, 4-n-butyl-phenol, 4-n-amyl-phenol, 4-tert-amyl-phenol, 4-n-hexyl-phenol, 4-n-heptyl-phenol, 2-methoxy-4-(2-propenyl)-phenol (Eugenol), 2-isopropyl-5-methyl-phenol (Thymol), mono- and poly-alkyl- and aralkyl-halophenols, methyl-p-chlorophenol, ethyl-p-chlorphenol, n-propyl-p-chlorophenol, n-butyl-p-chlorophenol, n-amyl-p-chlorophenol, sec-amyl-p-chlorophenol, n-hexyl-p-chlorophenol, cyclohexyl-p-chlorophenol, n-heptyl-p-chlorophenol, n-octyl-p-chlorophenol, o-chlorophenol, methyl-o-chlorophenol, ethyl-o-chlorophenol, n-propyl-o-chlorophenol, n-butyl-o-chlorophenol, n-amyl-o-chlorophenol, tert-amyl-o-chlorophenol, n-hexyl-o-chlorophenol, n-heptyl-o-chloropenol, p-chlorophenol, o-benzyl-p-chlorophenol, o-benzyl-m-methyl-p-chlorophenol, o-benzyl-m,m-dimethyl-p-chlorophenol, o-phenylethyl-p-chlorophenol, o-phenylethyl-m-methyl-p-chlorophenol, 3-methyl-p-chlorophenol, 3,5-dimethyl-p-chlorophenol, 6-ethyl-3-methyl-p-chlorophenol, 6-n-propyl-3-methyl-p-chlorophenol, 6-iso-propyl-3-methyl-p-chlorophenol, 2-ethyl-3,5-dimethyl-p-chlorophenol, 6-sec-butyl-3-methyl-p-chlorophenol, 2-iso-propyl-3,5-dimethyl-p-chlorophenol, 6-diethylmethyl-3-methyl-p-chlorophenol, 6-iso-propyl-2-ethyl-3-methyl-p-chlorophenol, 2-sec-amyl-3,5-dimethyl-p-chlorophenol, 2-diethylmethyl-3,5-dimethyl-p-chlorophenol, 6-sec-octyl-3-methyl-p-chlorophenol, p-bromophenol, methyl-p-bromophenol, ethyl-p-bromophenol, n-propyl-p-bromophenol, n-butyl-p-bromophenol, n-amyl-p-bromophenol, sec-amyl-p-bromophenol, n-hexyl-p-bromophenol, cyclohexyl-p-bromophenol, o-bromophenol, tert-amyl-o-bromophenol, n-hexyl-o-bromophenol, n-propyl-m,m-dimethyl-o-bromophenol, 2-phenyl-phenol, 4-chloro-2-methyl-phenol, 4-chloro-3-methyl-phenol, 4-chloro-3,5-dimethyl-phenol, 2,4-dichloro-3,5-dimethyl-phenol, 3,4,5,6-tetrabromo-2-methylphenol, 5-methyl-2-pentylphenol 4-isopropyl-3-methylphenol 5-chloro-2-hydroxydiphenyl-methane. Resorcinol and its derivatives, e.g. resorcinol, methyl-resorcinol, ethyl-resorcinol, n-propyl-resorcinol, n-butyl-resorcinol, n-amyl-resorcinol, n-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl-methane, 4'-chloro-2,4-dihydroxydiphenyl-methane, 5-bromo-2,4-dihydroxydiphenyl-methane, 4"-bromo-2,4-dihydroxydiphenyl-methane. Bisphenolic compounds, e.g. bisphenol A, 2,2'-methylene-bis-(4-chlorophenol), 2,2'-methylene-bis-(3,4,6-trichlorophenol) (hexachlorophene), 2,2'-methylene-bis-(4-chloro-6-bromophenol), bis-(2-hydroxy-3,5-dichlorophenyl)-sulfide, bis-(2-hydroxy-5-chlorobenzyl)-sulfide.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are Na2H2P2O7, Na4P2O7 and K4P2O7. Other suitable polyphosphates include hydrated or unhydrated alkali metal tripolyphosphates such as Na5P3O10 and K5P3O10.

In an embodiment of the invention the active ingredient comprises one or more Anti-gingivitis agents.

Anti-gingivitis agents can be antiinflammatory agents, such as salicylic acid derivatives (e.g. aspirin), paraminophenol derivative (e.g. acetaminophen), indole and indene acetic acids (indo-methacin, sulindac and etodalac), heteroaryl acetic acids (tolmetin, diclofenac and ketorolac), aryl propionic acid derivatives (ibuprofen, naproxen, ketoprofen, fenopren, oxaprozine), anthranilic acids-(mefenamic acid, meclofenamic acid), enolic acids (piroxicam, tenoxicam, phenylbutazone and oxyphenthatrazone), lactic acid bacteria (LAB), Osteopontin (ONP), IG-Lyt, hexefine, Aloe Vera, chlorhexedine, myrrh, or sage.

Anti-gingivitis agents also comprise psychotherapeutic agents, such as thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, or eldepryl.

In an embodiment of the invention, the active ingredient comprises one or more dental cosmetic ingredients.

A dental cosmetic ingredient includes a whitening agent. These are conveniently selected from teeth colour modifying substances that may be considered among the oral care actives useful in the tablet according to the invention. These substance are suitable for modifying the colour of the teeth to satisfy the consumer such as those listed in the CTFA Cosmetic Ingredient Handbook, 3.sup.rd Edition, Cosmetic and Fragrances Association Inc., Washington D.C. (1982), incorporated herein by reference. Specific examples include talc, mica, magnesium carbonate, calcium carbonate, calcium pyrophosphate, Baking soda, Icelandic moss, bamboo, sodium hexametaphosphate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical levels are from about 0.05% to about 20%, preferably from about 0.1% to about 15% and most preferably from about 0.25% to about 10%, by weight, of the composition.

Whitening agents for use herein may also comprise materials that remove or bleach intrinsic or extrinsic stains on or in tooth surfaces. Such substances are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. Additional bleaching substances may be hypochlorite, and chlorine dioxide. A preferred percarbonate is sodium percarbonate. Preferred persulphates are oxones. The content of these substances is dependent on the available oxygen or chlorine.

In embodiment of the invention the active ingredient comprises one or more abrasives.

Within the scope of the invention, the oral tablet may comprise abrasive. Typical materials include silica gels and precipitates, aluminas, phosphates, and mixtures thereof. Specific examples include dicalcium orthophosphate dihydrate, calcium pyrophosphate, Bamboo, tricalcium phosphate, hydrated alumina, beta calcium pyrophosphate, calcium carbonate, sodium polymetaphosphate, sodium hexametaphosphate, Calgen, Giltex, Quadrafos, Hagan phosphate, micromet, calcium phosphate dibasic, calcium monohydrogen phosphate, dicalcium orthophosphate secondary calcium phosphate, carbonic acid calcium salt, cacti, calcichew, calcidia, citrical, aragonite, calcite, valerite, aluminum oxide, alumina, silicon dioxide, silica, silicic anhydride, and resinous abrasive materials such as particulate condensation products of urea and formaldehyde and others such as disclosed in U.S. Pat. No. 3,070,510. Mixtures of polishing agents can also be used.

The silica polishing materials generally have an average particle size ranging between about 0.1 to about 30 microns; and preferably from about 5 to about 15 microns. The polishing agent can be precipitated silica or silica gels, such as the silica xerogels described in U.S. Pat. No. 3,538,230 or in U.S. Pat. No. 3,862,307. Preferred are the silica xeropgels marketed under the name "Syloid" by the W. R. Grace and Company, Davison Chemical Division. Also preferred are the precipitated silica materials such as those marketed by the J. M. Huber Corporation under the trade name "Zeodent", particularly the silica carrying the designation "Zeodent 119". The types of silica dental polishing agents useful in the tablet of the present invention are described in more details in U.S. Pat. No. 4,340,583. The polishing agents in the tablet according to the invention is generally present in the range from about 6% to about 70%, preferably from about 10% to about 50%, by weight of the tablet.

In an embodiment of the invention the oral tablet comprises one of more of the following active ingredients: anti-plaque agent, anti-gingivitis, dental cosmetic ingredient and/or abrasives in the amount of 0.1% to 35%, such as from 1% to 25% or such as from about 5% to about 10%, by weight of the oral tablet.

The content of these oral care ingredients in the oral tablet according to the invention is generally in the range from about 0.1% to about 35%, preferably from about 1% to about 25% and most preferably from about 5% to about 10%, by weight of the tablet.

Moreover, the invention relates to an oral tablet suitable for active pharmaceutical ingredients comprising a population of particles, the population of particles comprising directly compressible (DC) and non-directly compressible (non-DC) sugar alcohol particles, the tablet being designed to turn into liquid within 20 seconds of mastication.

Moreover, the invention relates to an oral tablet suitable for active pharmaceutical ingredients comprising a population of particles, the population of particles comprising directly compressible (DC) and non-directly compressible (non-DC) sugar alcohol particles, the tablet being designed to dissolve within 20 seconds of mastication.

Moreover, the invention relates to a medical device in tablet form comprising a population of particles, the population of particles comprising directly compressible (DC) and non-directly compressible (non-DC) sugar alcohol particles, the medical device for use in the alleviation or treatment of xerostomia.

Moreover, the invention relates to a medical device in tablet form comprising a population of particles, the population of particles comprising directly compressible (DC)

and non-directly compressible (non-DC) sugar alcohol particles, the medical device for use in alleviation or treatment of dysphagia.

Moreover, the invention relates to a method of providing induced saliva generation in the oral cavity, the method comprising the steps of:
i) providing an oral tablet comprising a population of particles, the population of particles comprising directly compressible (DC) and non-directly compressible (non-DC) sugar alcohol particles, and
ii) masticating the tablet and thereby generating saliva in the oral cavity induced by a plurality of discrete non-DC areas in the tablet.

Moreover, the invention relates to a method of alleviating or treating xerostomia, the method comprising the steps of:
i) providing an oral tablet comprising a population of particles, the population of particles comprising directly compressible (DC) and non-directly compressible (non-DC) sugar alcohol particles, and
ii) masticating the tablet and thereby alleviating or treating xerostomia.

Moreover, the invention relates to a method of alleviating or treating dysphagia, the method comprising the steps of:
i) providing an oral tablet comprising a population of particles, the population of particles comprising directly compressible (DC) and non-directly compressible (non-DC) sugar alcohol particles, and
ii) masticating the tablet and thereby generating saliva in the oral cavity,
iii) swallowing one or more pills together with induced saliva.

In an advantageous embodiment it is thereby possible to use the inventive oral tablet with a conventional tablet intended for swallowing by initially applying the inventive tablet for generation of saliva and then subsequently swallow the conventional oral tablet. The inventive tablet may thus compensate or counteract user's difficulties with conventional oral tablets in terms of swallowing.

In an embodiment of the invention, the step ii) of masticating the tablet involves masticating the tablet and thereby promoting fast release of active ingredients induced by a plurality of discrete non-DC areas in the tablet.

In an embodiment of the invention, step ii) of masticating the tablet involves masticating the tablet to release water soluble ingredients into saliva induced by a plurality of discrete non-DC areas in the tablet.

In an embodiment of the invention, step ii) of masticating the tablet involves releasing at least 50% by weight of the active ingredient within 20 seconds from onset of mastication.

BRIEF DESCRIPTION OF THE DRAWINGS

The invention will now be described with reference to the drawings where
FIGS. 1a and 1b shows an embodiment of the invention,
FIGS. 2a and 2b shows a two-module version of an embodiment of the invention,
FIGS. 3a and 3b shows a three-module version of an embodiment of the invention.

DETAILED DESCRIPTION OF THE INVENTION

Figure 4:
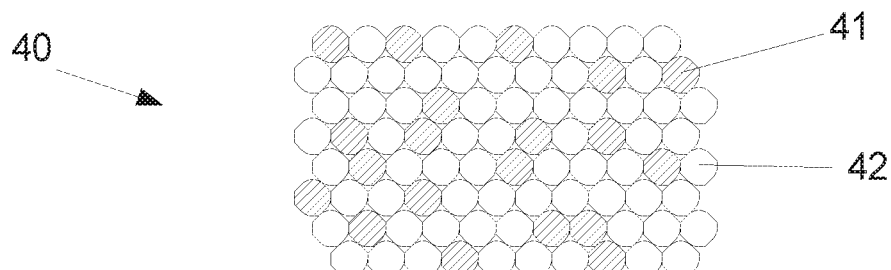
FIGS. 4 and 5 illustrates embodiments of the invention

As used herein the term "oral tablet" is considered as a tablet for oral use. Particularly, the oral tablet is considered as formed by tableting, i.e. compression of a particle composition, comprising the mentioned population of particles. Thus, the tablet is considered a compressed tablet formed by a plurality of particles. Typically, the oral tablet may also be referred to as a tablet.

In the present context the phrase "population of particles" refers to a statistical population of particles. The population of particles may be characterized by a number of different parameters, e.g. statistical parameters such as distribution of particles, average particle size, particle size distribution width, etc. The population of particles may have subpopulations, such as DC sugar alcohol particles, non-DC sugar alcohol particles, or in some embodiments particles comprising gum base. The phrasing "population of particles" may in an embodiment of the invention be provided as a plurality of tableted particles and where the population of particles are tableted in one module or it may refer to a population of particles where some of the particles are tableted into one module and other particles are tableted into another module.

In the present context, the term "non-DC areas" refers to small volumes or spaces formed during tableting from the non-DC particles of non-DC sugar alcohol. Moreover, each of the non-DC areas may be composed of a single non-DC sugar alcohol particle, or may comprise several non-DC sugar alcohol particles. When the non-DC areas are distinct, i.e. not diffuse, the non-DC areas may be evenly distributed in the tablet, or at least one module thereof when the tablet comprises two or more modules. In such embodiments, where the non-DC areas are evenly distributed in in the tablet, or at least one module thereof, the non-DC areas may thus facilitate an even saliva generation in the mouth upon mastication.

The term "non-DC sugar alcohol particles" refer to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol.

The term "DC sugar alcohol particles" refer to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC).

In the present context when the non-DC areas are referred to as "discrete" this signifies that the non-DC sugar alcohols are not continuously distributed, but present in the discrete areas corresponding to the discrete nature of the non-DC sugar alcohol particles.

In the present context, the term "suitable for active pharmaceutical ingredients" refers to the tablet as a suitable vehicle for e.g. inclusion and delivery of active pharmaceutical ingredients. However, it is noted that the tablet may or may not include active pharmaceutical ingredients or active ingredients.

When referring to induced saliva generation, it is noted that this induced saliva generation exceeds any saliva generation without the use of the tablet of the invention. Particularly, in an embodiment the induced saliva generation exceeds saliva generation when using conventional tablets without non-DC areas. Then, induced saliva generation is increased over any saliva generation associated with conventional products, e.g. by comparing with a tablet without non-DC sugar alcohol particles, or with a tablet where the discrete areas are based on DC sugar alcohol particles.

When referring to induced saliva generation, the saliva generation is tested using the following method.

Test subject abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 20 seconds. Then, saliva and any remains of the tablet is kept in the mouth within chewing for 10 second. 30 seconds after starting the test, the test subject discards saliva including any tablet fragments into a plastic cup, which is weighted. Saliva discarded also at 90 seconds after onset of mastication, at 180 seconds after onset of mastication, at 300 seconds after onset of mastication, at 420 seconds after onset of mastication, and at 600 seconds after onset of mastication. At all times, the test subject makes as little movement as possible, and refrains from swallowing.

As used herein, the term "particle size" refers to the average particle size as determined according to European Pharmacopoeia 9.1 when using test method 2.9.38 particle size distribution estimation by analytical sieving, unless otherwise specifically is mentioned.

As used herein the term "active ingredient" refers to a substance that is biologically active and has a physiological effect on the human body for the benefit of the human body or part thereof. Active ingredients include active pharmaceutical ingredients, but also other active substances such as nutraceuticals.

In the present context the term "release" refers to the released substance being liberated from the water-soluble matrix. In some embodiments, the process of releasing a substance corresponds to the substance being dissolved in saliva.

In the following raw materials will refer to the mixed particles to be compressed into a tablet according to embodiments of the invention unless otherwise stated.

The following description outlines explanations of how the tablet of the invention may be produced and further details of what may be added to the inventive composition.

Typically, the process of manufacture of the inventive tablet may be performed in a single tablet press, such as a rotary tablet press. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing of the tablets are performed at a force of 20 to 50 kN.

Important raw materials of the inventive tablet are non-DC sugar alcohol particles in combination with DC sugar alcohol particles.

The DC sugar alcohol particles refer to sugar alcohols known within the art as being direct compressible (DC).

The non-DC sugar alcohol particles refer to sugar alcohols known within the art as being non-directly compressible (DC).

According to a further embodiment of the invention, the applied non-DC sugar alcohol particles are best characterized as being non-directly compressible (non-DC). The use of non-DC sugar alcohols when compared to conventionally applied direct compressible sugar alcohol (DC) has shown remarkable effects to the user's perception of the delivery vehicle when chewed. This may partly be due to the somewhat larger size of non-DC sugar alcohol, when compared to DC sugar alcohol, but is may also be a result of a high content of sugar alcohol in the individual particles applied for compression. DC sugar alcohols, which for obvious reasons are marketed and applied for compression purposes, does not result in such improved salivation effect and mouthfeel.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Examples of a non-DC grade of erythritol includes Zerose™ erythritol 16952F supplied by Cargill. Further examples of non-DC sugar alcohol particles include non-DC xylitol as Xivia C from Dupont, non-DC isomalt as Isomalt GS from Beneo Paltinit, non-DC mannitol as Pearlitol from Roquette, non DC maltitol as Maltisorb. P200 from Roquette. Examples of a direct compressible (DC) grade of erythritol include Zerose™ DC 16966 also supplied by Cargill. Further examples of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab from Dupont.

Non-direct compressible (non-DC) sugar alcohols may include non-DC grades of Xylitol, non-DC grades of Erythritol, non-DC grades of Mannitol, non-DC grades of maltitol, non-DC grades of Lactitol, non-DC grades of Isomalt, or other suitable non-DC grades of sugar alcohols.

Direct compressible (DC) sugar alcohols may include sorbitol which is DC by nature, DC grades of Xylitol, DC grades of Erythritol, DC grades of Mannitol, DC grades of maltitol, DC grades of Lactitol, Isomalt or other suitable DC grades of sugar alcohols.

The present invention benefits from a synergy between the non-DC sugar alcohol particles and the DC sugar alcohol particles. The DC sugar alcohols may be e.g. sorbitol which is direct compressible by nature or it may be other sugar alcohols which has been preprocessed, e.g. by granulation with a suitable binder, to obtain particles which when compressed may encapsulate the non-DC sugar alcohol particles into a mechanically stable tablet. At the same time the non-DC sugar alcohol particles serves as a means for salivation which is both attractive to the user and also serves for the purpose of dissolving the DC sugar alcohol particles when the tablet is chewed as fast as possible.

According to embodiments of the invention, encapsulated flavors or active ingredients may be added to the final blend of raw materials prior to compression.

Different methods of encapsulating flavors or active ingredients, which may both refer to flavors or active ingredients mixed into the raw materials to be compressed into the oral tablet e.g. include spray drying, spray cooling, film coating, coascervation, Double emulsion method (Extrusion technology) or prilling.

Materials to be used for the above-mentioned encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Preferably, these ingredients should be added subsequent to any significant heating or mixing. In other words, the active ingredients should preferably be added immediately prior to the compression of the final tablet.

If applying the present invention in relation to chewing gum, the adding of active ingredients may be cautiously blended with pre-mixed gum base granulates and further ingredients such as the ingredients stipulated by the present claims, immediately prior to the final compression of the tablet.

In one embodiment the tablet according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetrone, Prometazin, Tropisetron, Brompheniramine, Ceterizin, leco-Ceterizin, Chlorcyclizine, Chlorpheniramin, Chlorpheniram, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabetsodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc, Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the tablet. The active agents, for which a controlled and/or accelerated rate of release is desired, are primarily substances with a limited water-solubility, typically below 10 g/100 mL inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from *ginseng*, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK(SO4) 2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Further examples of active ingredients include dental products including Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Further examples of active ingredients include Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride Further examples of active ingredients include vitamins. Vitamins include A, B1, B2, B6, B12, Folinic acid, Folic acid, niacin, Pantothenic acid, biotine, C, D, E, K. Minerals include Calcium, phosphor, magnesium, iron, Zinc, Copper, Iod, Mangan, Crom, Selene, Molybden. Other active ingredients include:

Q10®, enzymes. Natural drugs including *Ginkgo Biloba*, ginger, and fish oil.

Further examples of active ingredients include migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

In an advantageous embodiment of the invention the active ingredient is selected from active ingredients for the throat selected from acetylcysteine, ambroxol, amylmetacresol, benzocaine, bisacodyl, bismuth subsalicylate, bromhexine, cetirizine, cetylpyridinium, chlorhexidine, dextromethorphan hydrobromide, 2,4-dichlorobenzyl alcohol, doxylamine succinate, *eucalyptus* oil, flurbiprofen, glycerin, hexylresorcinol, lidocaine, menthol, myrrh, paracetamol, pectin, peppermint oil, phenol, phenylephrine, povidone-iodine, pseudoephedrine, ranitidine, simethicone, sodium docusate, spearmint, zinc, or any combination thereof; active ingredients for the gastrointestinal tract selected from alginate, atenolol, aspirin (acetylsalicylic acid), ampicillin, aminosalicylates, anhydrous citric acid, aspirin, bisacodyl, bismuth subsalicylate, bupropion, caffeine, calcium, calcium carbonate, cetirizine, cimetidine, cisapride, clarithromycin, desloratadine, dexlansoprazole, diphenhydramine HCl, diphenhydramine citrate, dimenhydrinate, docusate erythromycin, dopamine, esomeprazole, famotidine, fexofenadine HCl, guaifenesin, hydrotalcite, ibuprofen, ketoprofen, lactase enzyme, lansoprazole, loratadine, lorcaserin, loperamide, loperamide HCl, magnesium, magnesium carbonate, magnesium hydroxide, melatonin, methamphetamine HCl, metoclopramide, metronidazole, montelukast, mycostatin, naltrexone, naproxen, naproxen sodium, nizatidine, omeprazole, ondansetron, orlistat, pantoprazole, paracetamol (acetaminophen), pectin, phentermine HCl, polypodium leucotomos, prednisolone, prednisone, progesterone, propranolol, propantheline bromide, pseudoephedrine HCl, phentermine, rabeprazole, ranitidine, roflumilast, scopoloamine butyl hydroxide, simethicone, sodium, sodium bicarbonate, sodium docusate, sumatriptan, testosterone, tetracycline, topiramate, vitamin A, vitamin B, vitamin B12, vitamin C (ascorbic acid), vitamin D, and vitamin E, vitamin K, or any combination thereof, and active ingredients for buccal absorption selected from atenolol, baclofen, caffeine, carvedilol, chlorpheniramine, chlorpheniramine maleate, fluticasone propionate, maleate, desmopressin, diltiazem hydrochloride, doxylamine succinate, mycostatin, nicotine, nifedipine, nitroglycerin, omeprazole, ondansetron, oxymetazoline HCl, oxytocin, phenylephrine, piroxicam, prednisone, propranolol, salbutamol sulphate, scopoloamine butyl hydroxide, sumatriptan, triamcinolonacetonid, and any combination thereof.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

When including gum base in the formulation sugar alcohols typically constitute from about 5 to about 95% by weight of the tablet, more typically about 20 to about 80% by weight such as 30 to 70% or 30 to 60% by weight of the tablet.

In such an embodiment of the invention, the tablet further comprises, beside the already described sugar alcohols, materials selected from the group consisting of bulk sweeteners, flavors, dry-binders, tableting aids, anti-caking agents, emulsifiers, antioxidants, enhancers, absorption enhancers, buffers, high intensity sweeteners, softeners, colors, or any combination thereof.

Suitable sugar alcohols typically constitute from about 40 to about 99.9% by weight of the tablet, such as about 80 to about 99% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the tablet formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers and combinations thereof.

FIGS. 1a and 1b illustrates an embodiment of an oral tablet 10 according to an embodiment of the invention. FIG. 1a shows the oral tablet from the side and FIG. 1b shows the tablet from above.

Figure 5:
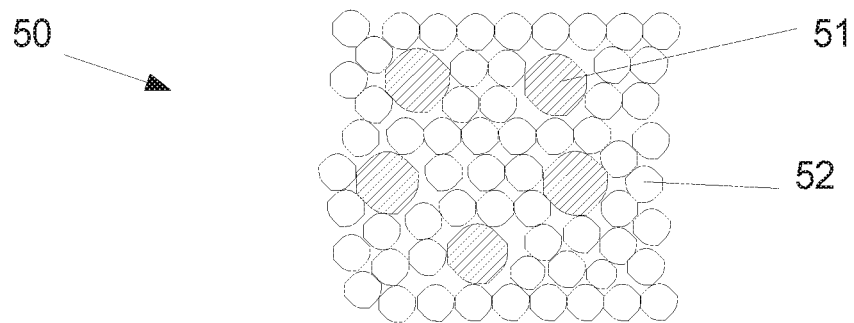

The composition and the way the tablet is or can be made is described elsewhere in the application and details regarding the structure and functioning of this tablet 10 is also indicated and explained further with reference to FIG. 4 and FIG. 5.

FIGS. 2a and 2b illustrates a two-module version of an oral tablet according to an embodiment of the invention. FIG. 2a shows the oral tablet from the side and FIG. 2b shows the tablet from above.

The composition and the way the tablet is made is described elsewhere in the application.

Figure 6:
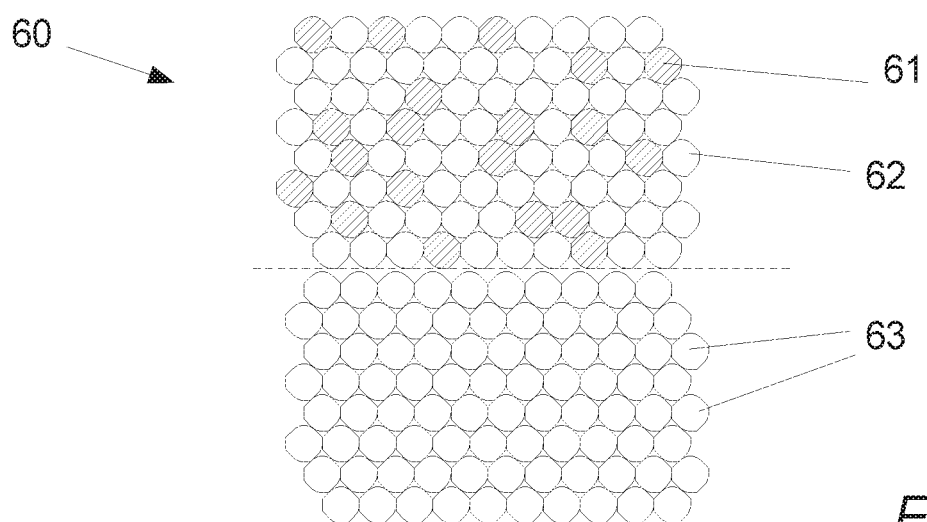
FIG. 6 illustrates a two-module version of an embodiment of the invention and where

Details regarding the structure and functioning of this tablet 10 is also indicated and explained further with reference to FIGS. 4, 5 and 6.

The intention with this illustration is to give an example of a physical form, which may be applicable within the scope of the invention. The intention is also to illustrate how the term "a module" is understood and applied throughout the description, i.e. that a module is referring to a population of a plurality particles and the particles have been tableted together to form a module. The term module is applied to indicate that one module comprises one population of tableted particles and another module comprises another population of tabled particles. A population of particles in the present context is thus understood to refer to a plurality of particles. A singular particle is thus of course not understood as a module.

Modules are typically, but not necessarily, distinguishable by the human eye, in particular if the applied compounds in the different modules are formed by differently colored population of particles or mixtures of particles.

The oral tablet 20 comprises an upper module 21 and a lower module 22. The modules, here in the shapes of layers, are thus physically distinct and each comprises a population of particles which have been tableted. The population of the different modules, 21 and 22, may typically be different for many purposes. Examples include use for visual conception, for mechanical purposes e.g. providing strength, for medical purposes, and of course also for maximizing the desired effect of non-DC sugar alcohol contained in the tablet.

In a preferred embodiment, most of the applied non-DC sugar alcohol(s) is comprised in the upper module 21 and the lower module 22 is mostly comprised of DC-components, i.e. components such as sugar alcohols, fillers, flavors, colors etc. conventionally used for direct compression. In embodiments of the invention, a first module, here the lower module 22 may be regarded and applied as a support module supporting another module, here the upper module 21. The benefit of this division in the designing of properties is that the module containing the non-DC sugar alcohol particles may comprises substantial amounts of non-DC sugar alcohol particles even in spite of the fact that the modules own mechanical strength is substantially weakened, as the supporting modules structural strength may be designed to ensure that the overall structural strength of the tablet is sufficient to obtain the desired friability and tablet appearance. This multi-modular design approach is of even more interest as the tablets designed according to this principle benefits, in terms of disintegration and dissolving of the tablet matrix during mastication of the tablet, from the increased salivation effect obtained from the applied high content of non-DC sugar alcohol particles in the relatively weak module.

FIGS. 3a and 3b illustrates a three-module version of an oral tablet 30 according to an embodiment of the invention. FIG. 3a shows the oral tablet 30 from the side and FIG. 3b shows the tablet from above.

The illustrated tablet 30 comprises an upper module 31, and intermediate module 33 and a lower module 32.

The upper module 31 may, as explained in relation to the upper module of FIGS. 2a and 2b, be formed by a population of particles comprising an effective amount of non-DC sugar alcohol particles. The intermediate layer may comprise further non-DC sugar alcohol particles and or a desired active ingredient.

The lower module 32 may comprise substantial amounts of DC-particles such as sugar alcohol(s), fillers, some binder and other relevant ingredients enabling the lower module 32 to form a structural support for at least the upper module 31.

FIG. 4 illustrates a part 40 of a cross-section of one of the oral tablets in FIG. 1-3. The part of the oral tablet, illustrated in FIG. 4 may thus correspond to a view of a part of the upper layers 21 or 31 or a part of the tablet 1.

Such part 40 of a tablet may within the scope of the invention comprise at least two different types of particles, namely non-DC sugar alcohol particles 41 and DC-particles 42. Preferred but non-limiting non-DC sugar alcohols are non-DC erythritol and non-DC xylitol as these non-DC sugar alcohols have shown effective to obtain the desired effect. The illustrated non-DC particles 41, although indicated on the figures with the same graphical expression may of course comprise non-DC sugar alcohol particles of the same type, but also comprise a mixture of two or more non-DC sugar alcohol particles.

The particles are evenly distributed amongst a plurality of DC particles 42 within the specified module. The DC particles 42, although indicated in the figure as same type particles may include different types of DC sugar alcohol particles, flavor particles, binders, etc. The intention with the figure is to illustrate that the non-DC sugar alcohol particles 41 in practice have to be homogenously distributed amongst the DC particles 42 in the final oral tablet 40. It may not be enough that the non-DC particles and DC particles are mixed homogenously at some stage during the preparation of the tableting process. The homogenous mix should preferably be maintained in the final oral tablet 40 in order to promote the desired effect and to obtain a mechanically stable tablet. A further advantageous effect of the evenly distributed non-DC sugar alcohol particles may be obtained through an advantageous and increased salivation during mastication of a tablet.

The understanding and conception of the evenly distribution of the non-DC sugar alcohol particles in the relevant tablet module may in practical terms be very difficult to define as such definitions are very difficult to monitor and control during the processing of the tablet but it has been possible to establish an industrial scale process, where the mixture containing the substantial amounts of non-DC sugar alcohol(s) may be established all the way through the process into the final tablet. Such process may e.g. be validated by test manufacturing of a sequence of tablets where the variation of the non-DC sugar alcohol content of the manufactured tablets are determined.

It is noted that the non-DC particles 41 forms small sub-areas or sub spaces in the final oral tablet or the relevant module of the final tablet, e.g. the upper modules 21 and 31. These sub-areas are elsewhere in the present application referred to as discrete non-DC areas and may be formed by single non-DC particles or very small groups of these non-DC particles. These discrete non-DC areas are thus intended to be contained within a matrix formed by DC-sugar alcohol particles or other DC-particles.

The non-DC areas, in the present embodiment, the non-DC sugar alcohol particles 41 are thus included in substantial amounts in the tablet and from a mechanical perspective supported and contained by the DC-particles 42 and together forming a matrix which, when chewed, may bring the non-DC sugar alcohol particles 42 into contact with the oral cavity and promote salivation. The promoted salivation, together with relatively weak mechanical structure of the module or tablet comprising the non-DC sugar alcohol particles induces a fast breakup of the tablet and thereby pushes the non-DC particles into contact with the oral cavity in a way which is completely different from compressed tablets made from DC-sugar alcohol particles, such as granulated erythritol or xylitol.

The non-DC areas may thus result in induced saliva generation upon mastication of the tablet and also induce and promote a very fast and pleasant dissolving of the tablet matrix when compared to conventional compressed tablets.

Active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this compensation may both compromise salivation effect and texture/mouth-feel during mastication.

FIG. 5 illustrates a part of a cross-section of one of the oral tablets in FIG. 1-3. The part of the oral tablet, illustrated in FIG. 5 may thus correspond a view of a part of the upper modules 21 or 31 or the tablet 1.

In terms of components applied, the tablet part illustrated in FIG. 5 may largely correspond to the above-described embodiment of FIG. 4, but now the tablet part comprises larger sized non-DC particles 51 containing in a compression of particles of DC particles 52.

The intention with the present FIG. 5 is merely to indicate that in particular the non-DC sugar alcohol particles may be larger in size than the DC particles and it is also noted in this context that the use of larger sized non-DC sugar alcohol particles may indeed increase the obtained salivation or the desired effect.

FIG. 6 illustrates a particular transition in a tablet 60 with two adjacent modules according to an embodiment of the invention. The presently illustrated part of such tablet may e.g. refer to the transition between the modules 21 and 22 of the tablet 20 as seen in FIG. 2a. The tablet 60 comprises non-DC sugar alcohol particles 61 and DC particles 62 in one module and another module comprising DC particles 63. The understanding of a module is here easily conceivable as the population of non-DC sugar alcohol particles 61 and DC particles 62 forms one module and the population of DC particles 63 forms another module. Often, the compositions of the DC sugar alcohol particles 62 and the DC sugar alcohol particles 63 may be different, depending on the specific circumstances.

Again, in relation to FIG. 5 and FIG. 6, active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this may compensation may both compromise salivation effect and texture/mouthfeel during mastication.

Particles comprising gum base, may also be present both as non-DC and DC particles, although DC-particles comprising gum base are highly preferred over non-DC gum base-containing particles. When applying particles comprising gum base, these particles are preferably but not necessarily included in a supporting module as DC particles 63 e.g. with mixed with sugar alcohol particles 63 as illustrated in FIG. 6.

The above illustrated modules are all designed as layers. It is stressed that other shapes of modules may be applicable within the scope of the invention. Non-limiting examples are modules having a sphere shape, diamond shape, oval shape, cone shape, etc. All the relevant shapes must of course be adapted to fit the tableting process according to known measures within the art.

EXAMPLES

Examples 1-38. Preparation of Two-Layer Tablets

TABLE 1A

Oral tablet compositions for first layer of bi-layer tablets containing variants of non-DC sugar alcohols. Amount are given in wt-% of the respective layer of tablet.

| Raw material (wt %) First layer | Ex1 | Ex2 | Ex3 | Ex4 | Ex5 | Ex6 |
|---|---|---|---|---|---|---|
| Non DC Xylitol | 50 | — | — | — | — | — |
| Sorbitol** | — | 50 | — | — | — | — |
| Non DC Isomalt | — | — | 50 | — | — | — |
| Non DC Erythritol | — | — | — | 50 | — | — |
| Non DC Mannitol | — | — | — | — | 50 | — |
| Non DC Maltitol | — | — | — | — | — | 50 |
| DC Isomalt | 43.75 | 43.75 | 43.75 | 43.75 | 43.75 | 43.75 |
| Sorbitol | — | — | — | — | — | — |
| Flavor | 4 | 4 | 4 | 4 | 4 | 4 |
| HIS | 0.25 | 0.25 | 0.25 | 0.25 | 0.25 | 0.25 |
| Magnesium Stearate | 1 | 1 | 1 | 1 | 1 | 1 |
| Binder HPC | 1 | 1 | 1 | 1 | 1 | 1 |
| Resistance to crunchiness [N]* | 160 | >350 | 190 | 142 | 90 | 174 |
| Friability | 0.74 | 0.25 | 0.63 | 1.30 | 1.45 | 1.00 |

*Method limitation means maximum resistance to crunch can be measured up to 350N..
**non-granulated sorbitol.

TABLE 1B

Oral tablet compositions for first layer of bi-layer tablets containing variants of non-DC sugar alcohols. Amount are given in wt-% of the respective layer of the tablet.

| Raw material (wt %) First layer | Ex7 | Ex8 | Ex9 | Ex10 | Ex11 | Ex12 |
|---|---|---|---|---|---|---|
| Non DC Xylitol | 50 | — | — | — | — | — |
| Sorbitol** | — | 50 | — | — | — | — |
| Non DC Isomalt | — | — | 50 | — | — | — |
| Non DC Erythritol | — | — | — | 50 | — | — |
| Non DC Mannitol | — | — | — | — | 50 | — |
| Non DC Maltitol | — | — | — | — | — | 50 |
| DC Isomalt | — | — | — | — | — | — |
| Sorbitol | 44.25 | 44.25 | 44.25 | 44.25 | 44.25 | 44.25 |
| Flavor | 4 | 4 | 4 | 4 | 4 | 4 |
| HIS | 0.25 | 0.25 | 0.25 | 0.25 | 0.25 | 0.25 |
| Magnesium Stearate | 1 | 1 | 1 | 1 | 1 | 1 |
| Binder HPC | 0.5 | 0.5 | 0.5 | 0.5 | 0.5 | 0.5 |
| Resistance to crunchiness [N]* | 190 | >350 | 270 | 170 | 120 | 210 |
| Friability | 0.65 | 0.12 | 0.87 | 1.13 | 1.25 | 0.88 |

*Method limitation means maximum resistance to crunch can be measured up to 350N.
**non-granulated sorbitol.

TABLE 2

Oral tablet compositions for the second layers of bi-layered tablets. Amount are given in wt-% of the respective layer.

| Rw material (wt %) Second layer | Ex1-12 | Ex13-24 | Ex25-36 |
|---|---|---|---|
| DC Maltitol | 94.75 | — | — |
| DC Xylitol | — | 94.75 | — |
| DC Isomalt | — | — | 94.75 |
| Flavor | 4 | 4 | 4 |
| HIS | 0.25 | 0.25 | 0.25 |
| Magnesium Stearate | 1 | 1 | 1 |

TABLE 3

Oral tablet compositions for bi-layered tablets containing variants of DC-sugar alcohols. Amount are given in wt-% of the respective layer.

| | Ex37 | Ex38 |
|---|---|---|
| Raw material (wt %) First layer | | |
| Non DC Erythritol | 50 | 50 |
| DC Isomalt | 43.75 | 43.75 |
| Sorbitol | — | — |
| Flavor | 4 | 4 |
| HIS | 0.25 | 0.25 |
| Magnesium Stearate | 1 | 1 |
| Binder HPC | 1 | 1 |
| Raw material (wt %) Second layer | | |
| DC Xylitol | — | — |
| DC Erythritol | 94.75 | — |
| DC Isomalt | — | — |
| DC Maltitol | — | — |
| DC Mannitol | — | 94.75 |
| Flavor | 4 | 4 |

TABLE 3-continued

Oral tablet compositions for bi-layered tablets containing variants of DC-sugar alcohols. Amount are given in wt-% of the respective layer.

|  | Ex37 | Ex38 |
|---|---|---|
| HIS | 0.25 | 0.25 |
| Magnesium Stearate | 1 | 1 |
| Resistance to crunchiness [N] | 140 | 182 |
| Friability | 1.25 | 1.68 |

Process Flow

The compositions indicated in the above Tables 1A and 1B and 2 are each processed into two-layer tablets with compositions as outlined in examples 1-12, 13-24 and 25-36. In other words, the examples 1-12 are bi-layer tablet with a first layer according to Table 1A and 1B and the second layer is based primarily on DC maltitol. In examples 13-24, the second layer is primarily based on Xylitol. In examples 25-36, the second layer is primarily based on DC isomalt as shown in Table 2.

The composition of Table 3 is likewise processed into corresponding two-layer tablets of each of the compositions as indicated examples 37 and 38.

For each example 1-38 the raw materials are sieved with a 1600 micron sieve and then weighed into the proper amount according to the exampled compositions of Tables 1A to 3.

The weighed amounts are then added to a Turbula mixer in a stainless steel container and blended at 50 rpm for 5 minutes. MgSt was added after 4 minutes of blending.

The mixtures are then tableted by means of a Piccola RIVA DC-SC-041-2 or a Fette 3090i.

The applied molds have circular cross sections with diameters of 16 mm and are hollowed to produce tablets, which are concave and/or curved. Evidently, other mold size and shapes may be applied within the scope of the invention.

The resulting tablets according to Examples 1-38 are then obtained by tableting with a suitable pressure force.

For each tablet of examples 1-38, the second layer as outlined in Table 2 and referred to as the second layer in Table 3 is pressed initially at a first relatively low pressure. The blended composition of the so-called first layer, i.e. compositions of Tables 1A and 1B and the first layer of Table 3 is then fed to the mold and a final two-layer tablet is then compressed at higher pressure than the pressure applied on the first layers, thereby producing final two-layer tablets according to Examples 1-38. It is noted that the final two-layer tablets of examples 1-38 are 1.8 grams tablets and that the first layer of the tablets weighs 0.9 and the second layer of the tablets weighs 0.9 gram.

A specification of relevant compounds applied in the examples explained above are listed below.
HPC: Hydroxy propyl cellulose. Klucel Nutra D from Ashland
Non DC Xylitol: Xivia C from Dupont
Non-granulated Sorbitol from PharmSorbidex from Cargill
Non DC Isomalt: Isomalt GS from Beneo Paltinit
Non DC Mannitol: Pearlitol from Roquette
Non DC Maltitol: Maltisorb. P200 from Roquette
Non DC Erythritol: Zerose 16952 from Cargill
DC Erythritol—Zerose 16966 from Cargill
DC Xylitol—Xylitab 200 from Dupont
DC Isomalt—Isomalt DC 101 from Beneo Paltinit
DC Mannitol—Pearlitol SD200 from Roquette
DC Maltitol—Sweetpearl 300 DC from Roquette Examples 39-41

TABLE 4

Compositions for 1.8 gram oral tablets. Amounts are given in wt-% of the tablet.

| Rw material (wt %) I layer | Ex39 | Ex40 | Ex41 |
|---|---|---|---|
| DC Isomalt | 45 | 35 | — |
| Non DC Erythritol | 48.75 | 43.75 | 48.75 |
| Non DC Maltitol | — | — | — |
| DC CaCO3 | — | 15 | 45 |
| Sorbitol | — | — | — |
| Flavor | 4 | 4 | 4 |
| HIS | 0.25 | 0.25 | 0.25 |
| Magnesium Stearate | 1 | 1 | 1 |
| Binder HPC | 1 | 1 | 1 |

All ingredients were received in powder form.
DC Isomalt—Isomalt DC 101 from Beneo Paltinit
Non DC Erythritol: Zerose 16952 from Cargill
HPC: Hydroxy propyl cellulose. Klucel Nutra D from Ashland
DC CaCO3: Scoralite 97 PVP from Scora Process Flow For each of the examples 39-41 the raw materials are sieved with a 1600 micron sieve and then weighed into the proper amount according to the exampled compositions of Table 4.

For each example the weighed amounts are then added to a Turbula mixer in a stainless steel container and blended at 50 rpm for 4 minutes and then adding magnesium stearate and blending one additional minute.

The resulting tablets according to Examples 39-41 are then obtained by tableting the mixtures by means of a Piccola RIVA DC-SC-041-2. A Fette 3090i may also applied.

Evaluation

TABLE 5

Sensory evaluation of Examples

| Ex | Total sensory experience Good/ Acceptable(Acc)/ Poor | Suitable Fast dissolving Chewable tablet | Initial Watering effect 1-5 1 low 5 high |
|---|---|---|---|
| 1 | Acc | A bit hard initial chew, disintegrate with crunchy feeling, many big particles for a long time | 4 |
| 2 | Poor | Unacceptable hard chew - not chewable or complete dissolvable within the first 30 seconds. | 2 |
| 3 | Poor | Very hard and difficult to disintegrate. Saliva increases but with many big non- dissolved particles though the first 30 sec. | 3 |
| 4 | Good | Nice crunchy fast dissolving tablet | 5 |
| 5 | Poor | Soft initial chew, different mouth feel. Sticky feeling. Does not dissolve fast enough or provide pleasant watering effect | 2 |

TABLE 5-continued

Sensory evaluation of Examples

| Ex | Total sensory experience Good/ Acceptable(Acc)/ Poor | Suitable Fast dissolving Chewable tablet | Initial Watering effect 1-5 1 low 5 high |
|---|---|---|---|
| 6 | Poor | Hard initial chew. Very crumble and sandy feeling. Salivation generation but sandy liquid feeling | 4 |

The above two-layer Examples 13-18 were evaluated according to three parameters by a test panel.

Two of the parameters were suitability as a chewable tablet and one parameter was the perceived watering effect. Due to the more complex nature of a two-layer tablet two further parameters were evaluated, namely resistance to crunching and friability.

It was first of all noted that the watering effect was considered relatively high for examples 13, 15, 16 and 18, i.e. the examples based on non-DC Xylitol, non-DC Isomalt, non-DC Erythritol and non-DC Maltitol. The watering effect is considered to be representative or equal to the elsewhere described salivation effect.

The test panel clearly indicated that the overall chewing process and the mouthfeel was no less than impressive in relation to Example 16 based on non-DC Erythritol. It was also noted that the test panel identified non-DC Xylitol of example 13 and non-DC Maltitol of example 18 as having an impressive watering effect when compared to e.g. the sorbitol based example.

As a supplement to the sensory evaluation, the resistance to crunching and friability was measured and indicated in the Examples 13-24, i.e. with reference to a bi-layer tablet with a first layer as indicated in Table 1A and Table 1B and a second layer based primarily on DC xylitol as indicated in Table 2.

The resistance to crunching is determined according to European Pharmacopoeia 9.1, test method 2.9.8. by using a pharmaceutical resistance to crunching tester model Pharma Test type PTB 311.

Friability is measured according to European Pharmacopoeia 9.1, test method 2.9.7. by using a pharmaceutical friability-tester PTF 10E from Pharma Test.

Figure 7:
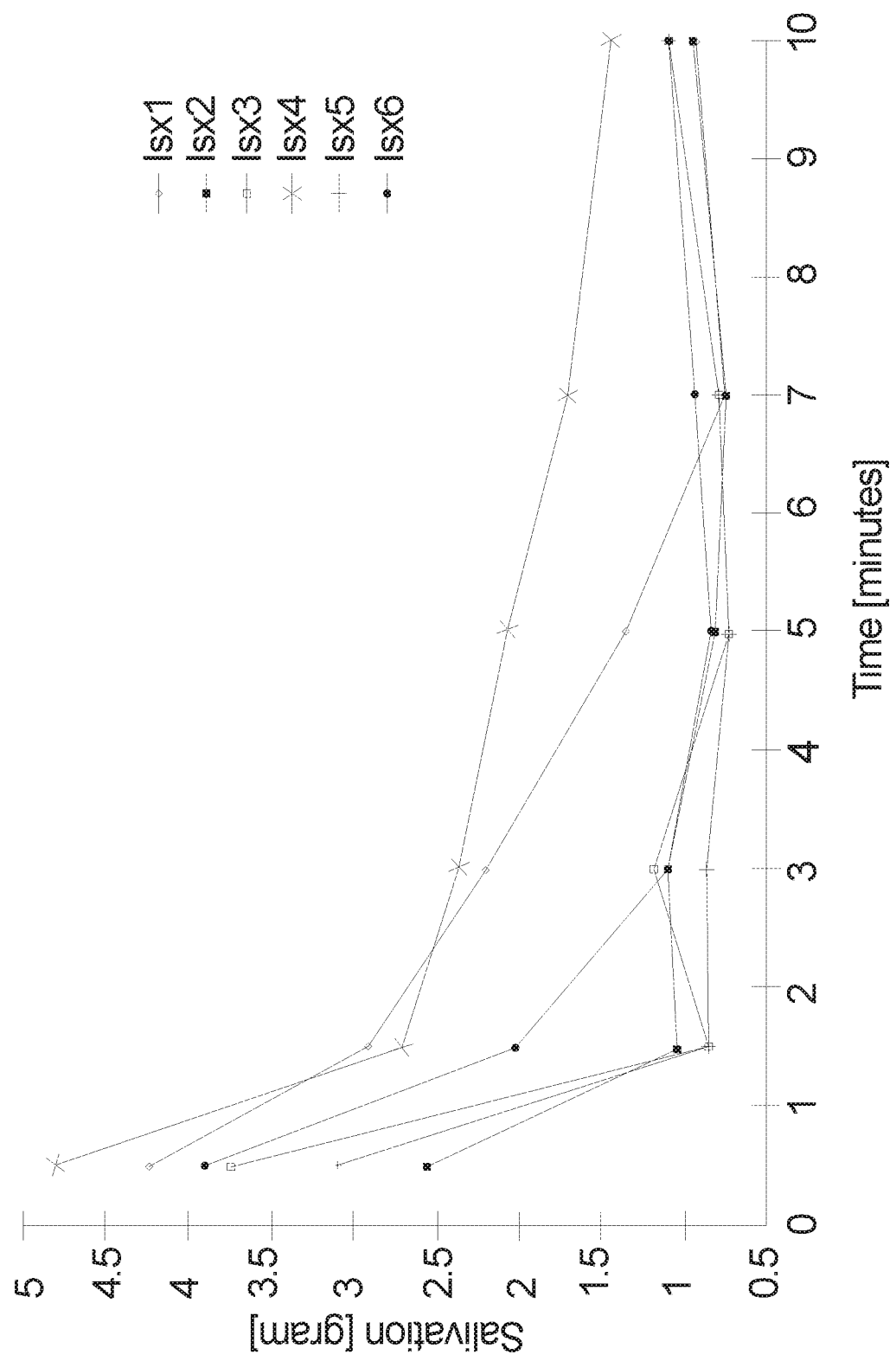
FIG. 7 illustrates the short and long-term effect of salivation obtained through different types of non-DC sugar alcohols.

FIG. 7 illustrates a measuring of the salivation effect related to the above-mentioned Examples 13-18, where different non-DC sugar alcohols have been applied. Sorbitol is applied as a reference as a representative DC sugar alcohol.

ISX1 refers to the non-DC xylitol example 13,
ISX2 refers to the sorbitol example 14,
ISX3 refers to the non-DC isomalt example 15,
ISX4 refers to the non-DC erythritol example 16,
ISX5 refers to the non-DC mannitol example 17 and
ISX6 refers to the non-DC maltitol example 18.

The saliva generation as measured with reference to FIG. 7 and the associated examples is defined in the description as a definition with reference to the measuring method.

The results of the measured saliva generation are illustrated in FIG. 7, where saliva generation in measured in grams as a function of time (minutes).

It is noted that the saliva generation from all non-DC sugar alcohols are impressive in the beginning, but it is also noted that saliva generation over time is no less than astonishing in relation to ISX4, i.e. the non-DC erythritol example 16. It is thus noted that the salivation effect is increased a very long time after the major part of non-DC erythritol based tablet has been swallowed or collected during the measurement. It is also observed that the relatively low initial perceived salivation effect of example 14, i.e. the sorbitol based example is confirming the sensory evaluation as mentioned above.

What is claimed is:

1. An oral tablet suitable for active pharmaceutical ingredients comprising a population of particles, the population of particles comprising sugar alcohol particles in a grade that is intended for direct compression (DC sugar alcohol particles) and sugar alcohol particles in a grade that is not intended for direct compression (non-DC sugar alcohol particles), the non-DC sugar alcohol particles being separate particles in the tablet, the non-DC sugar alcohol particles providing the tablet with a plurality of discrete non-DC areas formed by single non-DC sugar alcohol particles or small groups of non-DC sugar alcohol particles distributed between the DC sugar alcohol particles, and the non-DC areas resulting in induced saliva generation upon mastication of the tablet.

2. The oral tablet according to claim 1, wherein the non-DC areas are evenly distributed in the tablet or at least one module of the tablet.

3. The oral tablet according to claim 1, wherein a series of at least 10 of said tablets comprises said non-DC particles in an amount varying with a relative standard deviation (RSD) below 10%.

4. The oral tablet according to claim 1, wherein the tablet is a chewable tablet.

5. The oral tablet according to claim 1, wherein the non-DC sugar alcohol particles are non-DC particles of erythritol, or maltitol, or xylitol, or isomalt, or lactitol, or mannitol, or combinations thereof.

6. The oral tablet according to claim 1, wherein the tablet comprises said non-DC sugar alcohol particles in an amount of at least 10% by weight of the tablet.

7. The oral tablet according to claim 1, wherein said DC sugar alcohol particles are DC particles of sorbitol, or erythritol, or xylitol, or lactitol, or maltitol, or mannitol, or isomalt, or combinations thereof.

8. The oral tablet according to claim 1, wherein friability of the tablet is less than 3% measured according to European Pharmacopoeia 9.1, test method 2.9.7. using a pharmaceutical friability-tester PTF 10E from Pharma Test.

9. The oral tablet according to claim 1, wherein the tablet has a weight ratio between said non-DC sugar alcohol particles and said DC sugar alcohol particles that is between 0.3 and 0.7.

10. The oral tablet according to claim 1, wherein the tablet generates more than 1.5 mL saliva within 30 seconds from onset of mastication.

11. The oral tablet according to claim 1, wherein the tablet generates more than 1.5 mL saliva within a period from 30 to 90 seconds from onset of mastication.

12. The oral tablet according to claim 1, wherein the oral tablet comprises tooth paste in the amount of at least 0.1% by weight of the oral tablet.

13. The oral tablet according to claim 1, wherein the oral tablet comprises dentifrice in the amount of at least 0.1% by weight of the oral tablet.

14. A medical device in tablet form comprising a population of particles, the population of particles comprising sugar alcohol particles in a grade that is intended for direct compression (DC sugar alcohol particles) and sugar alcohol particles in a grade that is not intended for direct compression (non-DC sugar alcohol particles), the non-DC sugar alcohol particles being separate particles located as single non-DC sugar alcohol particles or small groups of non-DC sugar alcohol particles between the DC sugar alcohol particles in the tablet, the medical device for use in the alleviation or treatment of xerostomia.

15. A medical device in tablet form comprising a population of particles, the population of particles comprising sugar alcohol particles in a grade that is intended for direct compression (DC sugar alcohol particles) and sugar alcohol particles in a grade that is not intended for direct compression (non-DC sugar alcohol particles), the non-DC sugar alcohol particles being separate particles located between the DC sugar alcohol particles in the tablet, the medical device for use in alleviation or treatment of dysphagia.

16. The oral tablet according to claim 1, wherein the non-DC sugar alcohol particles comprise non-DC particles of erythritol.

17. The oral tablet according to claim 1, wherein the non-DC sugar alcohol particles comprise non-DC particles of maltitol.

18. The oral tablet according to claim 1, wherein the non-DC sugar alcohol particles comprise non-DC particles of xylitol.

19. The oral tablet according to claim 1, wherein at least 30% by weight of the non-DC sugar alcohol particles have a particle size above 500 µm.

* * * * *